United States Patent [19]
Gasser

[11] Patent Number: 4,720,319
[45] Date of Patent: Jan. 19, 1988

[54] METHOD FOR APPLYING RETENTION MEANS ONTO CASTING PATTERNS OF DENTAL PROSTHETIC METAL CONSTRUCTIONS

[75] Inventor: Oswald Gasser, Seefeld, Fed. Rep. of Germany

[73] Assignee: ESPE Fabrik pharmazeutischer Praparate GmbH, Fed. Rep. of Germany

[21] Appl. No.: 853,033

[22] Filed: Apr. 17, 1986

[30] Foreign Application Priority Data

Apr. 19, 1985 [DE] Fed. Rep. of Germany ....... 3514283

[51] Int. Cl.$^4$ .............................................. B32B 31/28
[52] U.S. Cl. .............................. 156/273.5; 156/275.5; 156/275.7; 156/297; 156/307.7; 156/332; 430/285; 430/320; 433/206; 433/223
[58] Field of Search ............... 156/273.5, 275.5, 275.7, 156/297, 332, 307.7; 264/19; 433/206, 209, 223, 34; 430/285, 320

[56] References Cited

U.S. PATENT DOCUMENTS

| | | | |
|---|---|---|---|
| 3,367,027 | 2/1968 | Kato | 433/206 |
| 3,658,620 | 4/1972 | Hall | 156/273.5 |
| 3,666,591 | 5/1972 | Hall | 156/273.5 |
| 4,022,674 | 5/1977 | Rosen | 156/273.5 |
| 4,555,389 | 12/1985 | Ueno et al. | 264/19 |
| 4,642,244 | 2/1987 | Tripp et al. | 156/273.5 |

FOREIGN PATENT DOCUMENTS 3429119  2/1986  Fed. Rep. of Germany ...... 433/223

*Primary Examiner*—Jerome Massie
*Attorney, Agent, or Firm*—Birch, Stewart, Kolasch & Birch

[57] ABSTRACT

Completely removable retention means are applied onto casting patterns for dental prosthetic metal constructions by coating the casting pattern with an adhesive coating composition to hold said retention means in position, said composition containing at least one photopolymerizable compound the polymerization of which is inhibited by oxygen, and at least one photopolymerization initiator, irradiating the coated casting pattern, applying the retention means, and irradiating the casting pattern once more.

14 Claims, No Drawings

METHOD FOR APPLYING RETENTION MEANS ONTO CASTING PATTERNS OF DENTAL PROSTHETIC METAL CONSTRUCTIONS

BACKGROUND AND FIELD OF THE INVENTION

The invention relates to a method for applying retention means onto casting patterns of dental prosthetic metal constructions.

Normally teeth missing to a substantial degree are replaced by a metal construction in the form of a crown or bridge. For cosmetic reasons the portion of the metal construction visible in the mouth is covered at least partially by a composition having the color of natural teeth. Besides ceramic compositions, special synthetic materials are used for this purpose. In order to firmly anchor the synthetic material to the metal construction, the surface of the metal construction is provided with so-called retention means. Normally these retention means are small beads (of 0.2 to 0.8 mm diameter, for example) but also, specially fitted pieces of honeycomb and grid structures are employed.

Such retention means, on the one hand, offer improved adhesion owing to the enlarged surface area, while at the same time they prevent detachment of the synthetic resin facing under tensile, shear, or compressive stress by virtue of their cross section which tapers towards the metal construction.

The metal constructions are produced according to the lost wax casting technique. For this purpose the configuration of the prosthetic metal construction is modelled in wax on a plaster model of the dentition. This so-called casting pattern is then embedded in a refractory mold, the wax is removed by melting or burning, and the liquid metal is introduced in a manner known per se.

It has proved impractical to model the rentention means in wax, because undercuts pose a modelling problem, and this procedure is time-consuming and awkward.

It has been known to first apply an adhesive to the wax surface and then to place, on the adhesive, synthetic resin beads, or grid or honeycomb structures of wax or plastic, which are removable completely thereafter e.g. by burning or melting. The casting pattern can then be embedded as usual, the wax and the retention bodies can be removed, and the liquid metal can be poured in.

This method leaves relatively little time to apply the retention means, since the adhesives dry after a short time and are no longer sticky. Therefore, careful and proper distribution of the retention means over the surface of the casting pattern is frequently not possible.

If the adhesive layer is too thick—due to or promoted by a dried-up adhesive mix—the retention bodies can partially sink into the adhesive up to more than their maximum diameter. Hence, the required extent of surface enlargement is not attained. However, it is even more detrimental that above the casting surface there extend only few or no parts of the retention means whose cross section tapers toward the surface of the casting pattern. It will be easily understood that these shortcomings greatly reduce the adhesion of the plastic facing to the metal surfaces.

In addition, for cosmetic reasons it is normally necessary to cover the metal construction with a so-called opacifier before applying the synthetic resin facing material, i.e. to cover the metal color by an opaque film having a color similar to that of teeth. Frequently these opacifier compositions have less strength than the synthetic resin facing material. Also, after application of the opacifier material in a thickness covering the substrate, undercuts at the retention means must still be available which can be filled by the synthetic facing material. For this reason, it is desirable that, as far as possible, the retention means be anchored to the metal surface only punctually, leaving a maximum downwardly tapering portion of the retention means which is available for adhesion of opacifier compositions and synthetic facing material.

SUMMARY OF THE INVENTION

Therefore, it is an object of the invention to provide a method in which the retention means are applied on casting patterns in such a way that the portions of the retention means tapering toward the model surface extend substantially completely above the surface of the model.

DETAILED DESCRIPTION OF THE INVENTION

The above-discussed problems are solved by the process of the invention, wherein:

1.1 the casting pattern is coated with a completely removable fluid adhesive composition containing
  (a) at least one photopolymerizable compound whose polymerization is inhibited by oxygen,
  (b) at least one photopolymerization initiator,
  (c) optionally at least one photopolymerization activator, and
  (d) optionally fillers, coloring agents and adjuvants,
1.2 the coated casting pattern is irradiated by means of a suitable light source,
1.3 the completely removable retention means are applied onto the irradiated surface of the casting pattern, and
1.4 the casting pattern is again irradiated.

In step 1.1 of the method, the casting pattern can be coated with adhesive composition in the desired areas by brushing, spraying, or dipping.

Irradiation in step 1.2 of the method cures the photopolymerizable composition, while the surface forms a tacky layer due to inhibition by oxygen. On this layer, the desired retantion means of plastic or wax are applied.

Further irradiation with light from a suitable light source then cures the areas at the contact faces of the retention bodies which are no longer accessible to oxygen, so that the retention means are reliably held in position.

Thereafter the casting pattern is embedded, as usual, in a refractory composition, the casting pattern is removed by heating, and metal casting is performed.

In the method of the invention the inhibited layer of the adhesive lacquer is stable for nearly an unlimited time after the first irradiation, and the dental technician can deliberately distribute individual retention beads over particularly critical areas by means of a pair of tweezers. Only the subsequent second irradiation fastens the retention beads so that during this work corrections are still possible. Moreover, any incomplete work can be easily interrupted and resumed after some time.

Suitable photopolymerizable compounds whose polymerization at the surface is inhibited by atmospheric oxygen are ethylenically unsaturated compounds polymerizing by free radicals, e.g. unsaturated polyester resins in mixture with styrene or vinyl toluene, vinyl ethers, allyl esters, and especially derivatives of acrylic and methacrylic acid.

Among the derivatives of acrylic and methacrylic acid the esters with mono-, di-, or polyfunctional alcohols have proved especially suitable. Also the so-called urethane acrylates and methacrylates are suitable.

The use of difunctional acrylates or methacrylates is especially preferred.

Suitable photopolymerization initiators are the conventional photopolymerization initiators such as aromatic monoketones, thioxanthones, aromatic and aliphatic 1,2-diketones, benzoine ethers, benzil ketals, and phosphine oxides and phosphine sulfides.

The photopolymerization initiators responding to visible light of a wavelength between 400 and 550 nm are especially well suited. Photopolymerization initiators suitable in this range are, for example, thioxanthones, 1,2-diketones, and phosphine oxides, and phosphine sulfides. Among the 1,2-diketones, camphor quinone, benzil, and phenanthrene quinone are especially suited.

The photopolymerization initiators are used in the customary concentrations, i.e., 0.01 to 10% by weight, based on the polymerizable compounds.

The photopolymerization initiators are advantageously used together with known photopolymerization activators. Suitable photopolymerization activators are organic amines, especially tertiary amines, cyclic 1,3-diketones such as barbituric acids, and 2-substituted 1,3-cyclopentanediones and 1,3-cyclohexanediones, as well as organic phosphites.

Also the photopolymerization activators are used in the customary concentration, i.e. 0.01 to 10% by weight, based on the polymerizable compounds.

The adhesive coating compositions used for the method of the invention may contain organic fillers or soluble organic polymers for adjustment of the flow properties and of the viscosity.

To the adhesive coating compositions, substances can be added which promote wetting of the casting pattern. Also, pigments or dyestuffs must be selected such that they do not have a high self-absorption in the range where the photopolymerization initiators employed have their active light absorption. Moreover, the adhesive coating compositions may contain conventional stabilizers against premature thermal polymerization.

The components of the photopolymerizable adhesive coating compositions must be selected such that the polymer can be removed completely from the embedding composition without leaving any residues, e.g. by burning or melting, before casting is commenced.

The thickness of the top layer of the photopolymer inhibited by the atmospheric oxygen can be found by the expert in a few simple tests in which the following factors are significant:
reactivity and oxygen-sensitivity of the monomers
activity of the photopolymerization initiator and of the photopolymerization activator, if any
concentration of the photopolymerization initiator or of the photopolymerization activator, if any
intensity of the light source.

EXAMPLE

The following phoopolymerizable composition is prepared:

In a mixture of
41 grams bishydroxymethyl bicyclo-[5.2.1.0$^{2,6}$]-decanediacrylate
30 grams bis-GMA (reaction product of glycidyl methacrylate and bisphenol A)
12 grams ethylene glycol dimethacrylate, and
8 grams methyl methacrylate
there are dissolved
0.9 gram camphor quinone
1.0 gram methyl diethanolamine dimethacrylate, and
0.01 gram blue fat-soluble dye.

With a brush, a thin film of this solution is applied onto a casting pattern of wax and is irradiated with a commercial daylight polymerization device (Visio-Alfa, a product of Messrs. Espe) for about 10 seconds over the whole area.

Commercially available retention beads made of plastic (0.4 mm diameter) are uniformly strewn over the tacky surface layer. Several retention beads are picked up with a tapering brush of marten hair and are deliberately planted in the marginal region.

Thereafter the casting pattern is irradiated once more with the above mentioned radiator for about 10 seconds.

The retention beads now adhere well to the surface of the casting pattern. They are fastened merely at their point of contact and therefore have major areas tapering toward the pattern surface.

Thereafter the casting pattern is embedded into a refractory mold, the wax model with the retention beads is removed by heating, and metal casting is performed.

In this way a metal construction is obtained which has well shaped retention beads at the surface which are fastened only at the point of contact and which offer useful surfaces tapering toward the metal surface.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for applying removable retention means onto casting patterns of dental prosthetic metal constructions comprising:
    (a) coating a wax casting pattern with a fluid adhesive composition comprising at least one photopolymerizable compound the polymerization of which is inhibited by oxygen, and at least one photopolymerization initiator;
    (b) irradiating said casting pattern;
    (c) applying removable retention means onto the irradiated surface of said casting pattern; and
    (d) irradiating said casting pattern.

2. The method according to claim 1, wherein said photopolymerizable compound is an ethylenically unsaturated compound capable of undergoing free radical photopolymerization.

3. The method according to claim 2, wherein said photopolymerizable compound is an unsaturated polyester in mixture with styrene or vinyl toluene, a vinyl ether, or an allyl ester.

4. The method according to claim 2, wherein said photopolymerizable compound is an acrylic or methacrylic acid derivative.

5. The method according to claim 2, wherein said photopolymerizable compound is an ester of acrylic or methacrylic acid.

6. The method according to claim 1, wherein said fluid adhesive composition further contains at least one photopolymerization activator.

7. The method according to claim 6, wherein said fluid adhesive composition further contains fillers and coloring and adjuvant substances.

8. A method for applying removable retention means onto casting patterns of dental prosthetic metal constructions comprising:
(a) coating a wax casting patterns with a fluid adhesive composition comprising at least one photopolymerizable compound the polymerization of which is inhibited by oxygen, and at least one photopolymerization initiator;
(b) irradiating said casting pattern to cure said photopolymerizable composition while forming a tacky surface layer due to inhibition by oxygen;
(c) applying removable retention means onto the irradiated surface of said casting pattern; and
(d) irradiating said casting pattern to cure the photopolymerizable composition at the contact faces of the retention bodies inaccessible to oxygen for fastening said retention means.

9. The method according to claim 8, wherein said photopolymerizable compound is an ethylenically unsaturated compound capable of undergoing free radical photopolymerization.

10. The method according to claim 9, wherein said photopolymerizable compound is an unsaturated polyester in mixture with styrene or vinyl toluene, a vinyl ether, or an allyl ester.

11. The method according to claim 9, wherein said photopolymerizable compound is an acrylic or methacrylic acid derivative.

12. The method according to claim 9, wherein said photopolymerizable compound is an ester of acrylic or methacrylic acid.

13. The method according to claim 8, wherein said fluid adhesive composition further contains at least one photopolymerization activator.

14. The method according to claim 13, wherein said fluid adhesive composition further contains fillers and coloring and adjuvant substances.

* * * * *